United States Patent [19]

Meyer

[11] 3,996,289
[45] Dec. 7, 1976

[54] PROCESS FOR THE PREPARATION OF 2-NITROBENZALDEHYDE

[75] Inventor: Horst Meyer, Wuppertal, Germany

[73] Assignee: Bayer Aktiengesellschaft, Germany

[22] Filed: Mar. 11, 1975

[21] Appl. No.: 557,297

[30] Foreign Application Priority Data

Mar. 28, 1974 Germany .......................... 2415061

[52] U.S. Cl. ............................ 260/599; 260/515 R
[51] Int. Cl.$^2$ ........................................ C07C 51/16
[58] Field of Search ................................... 260/599

[56] References Cited

OTHER PUBLICATIONS

Reissert, Ber. Deut. Chem. Ges., vol. 30 (1897) pp. 1030–1053.

*Primary Examiner*—Bernard Helfin

[57] ABSTRACT 2-nitrobenzaldehyde, a valuable chemical intermediate, is prepared through the oxidation of an alkali metal salt of 2-nitrophenylpyruvic acid with potassium permanganate in an alkaline medium. Advantageously the requisite starting material is prepared directly by the reaction of 2-nitrotoluene and a diester of oxalic acid in the presence of an alcoholate and is then subjected to the oxidation without isolation. In a preferred embodiment the oxidation reaction mixture is acidified to convert the manganese-(IV) oxide to soluble manganese-(II) salts with concurrent conversion of oxalic acid to carbon dioxide. The process is industrially attractive in terms of the high yield, the availability of starting material and the ease of the manipulative steps involved.

6 Claims, No Drawings

PROCESS FOR THE PREPARATION OF 2-NITROBENZALDEHYDE

DETAILED DESCRIPTION

The present invention relates to a process for the production of 2-nitrobenzaldehyde, a valuable intermediate as for example in the preparation of pharmaceutically active 4-(2'-nitrophenyl)-1,4-dihydropyridine derivatives.

2-nitrobenzaldehyde is a known compound which is difficult to obtain, see e.g., L. F. and M. Fieser, Organische Chemie, Verlag Chemie, Weinhem (1968), page 1,004. One recommended method of synthesis is the nitration of cinnamic acid or its esters; see e.g., J. Chem. Soc. (London) 1950, 204, separation of the resulting isomer mixture of 4- and 2-nitrocinnamic acids and subsequent oxidation of 2-nitrocinnamic acid with potassium permanganate in accordance with the following equations:

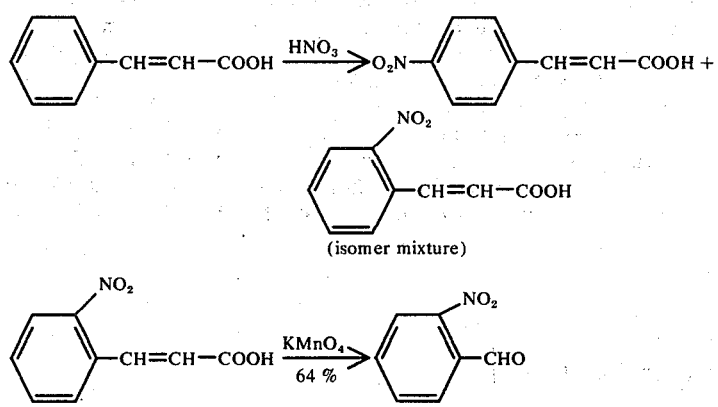

Since, however, at most 40% of 2-nitrocinnamic acid can be isolated in the course of the expensive separation of the isomers, the overall yield of this process, namely approximately 25%, is not satisfactory. Furthermore, in this process the yield of 64% in the oxidation stage can only be achieved when using very dilute solutions; e.g. 5 g/1,000 ml.

The problem of separating the isomers can be circumvented, according to another process, by using 2-nitrophenylpyruvic acid, which is easily accessible by condensation of 2-nitrotoluene and diesters of oxalic acid, see e.g., A Reissert, Ber. dtsch. Chem. Ges. 30, 1031 (1897). According to this method, 2-nitrophenylpyruvic acid when treated with potassium permanganate in dilute solution yields 2-nitrobenzoic acid as the main product, accompanied by a maximum of only 33% of 2-nitrobenzaldehyde:

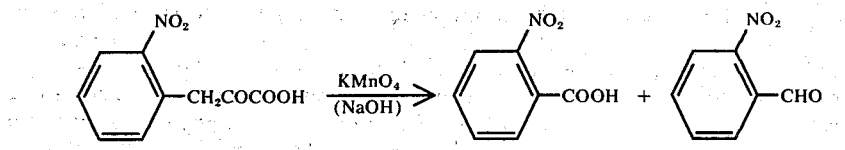

Reissert noted that in no way did it prove possible to obtain the aldehyde as the main product.

The unsubstituted phenylpyruvic acid similarly can only be converted to benzaldehyde in 14% yield; see e.g., Liebigs Ann. Chem. 462, 138, 146.

In accordance with the present invention, a 2-nitrobenzaldehyde of the formula

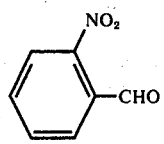  (I)

can be obtained in high purity and good yields if an alkali metal salt of 2-nitrophenylypyruvic acid of the formula:

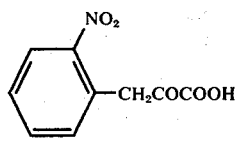  (IV)

is oxidized with potassium permanganate in alkaline aqueous solution at temperatures from about −10° to about +50° C. Following the oxidation, the solution can be acidified with advantageous results, described below.

It is rather surprising that 2-nitrobenzaldehyde is produced in such good yield by this process since from the state of the art, 2-nitrobenzoic acid would be expected to be the main product.

The alkali metal salt of 2-nitrophenylpyruvic acid may be obtained by reacting 2-nitrotoluene of the formula:

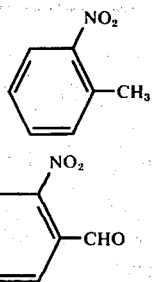  (II)

with an oxalic acid diester of the formula:

(COOR)$_2$  (III)

wherein R is a lower alkyl or aralkyl group. Since the R group does not enter into the reaction and is saponified in the course of this preparation, its nature is not critical. When the 2-nitrophenylpyruvic acid as a salt is so prepared, it is not necessary to isolate it before subjecting it to the oxidation reaction in accordance with the invention, which is also conducted under basic conditions.

The process according to the invention has a number of advantages. Thus, the starting products, 2-nitrotoluene and oxalic acid diesters, are readily available and inexpensive. The requisite starting material, an alkali metal salt of 2-nitrophenylpyruvic acid, can be conveniently synthesized as an intermediate product and then treated without isolation so that the process is easy to carry out industrially. Acidification of the resulting reaction mixture after the last oxidation stage (IV → I) gives oxalic acid, which reduces the voluminous manganese-(IV) oxide, which has precipitated, to give soluble manganese-(II) salts and is itself oxidized to gaseous carbon dioxide. This avoids the filtration and adsorption problems usually caused by manganese dioxide. Moreover, the potassium permanganate can be introduced in solid form so that the volume yield is improved decisely compared to prior art methods.

If 2-nitrotoluene, oxalic acid dimethyl ester and potassium methylate are used as starting materials, the course of the reaction can be represented by the following equations:

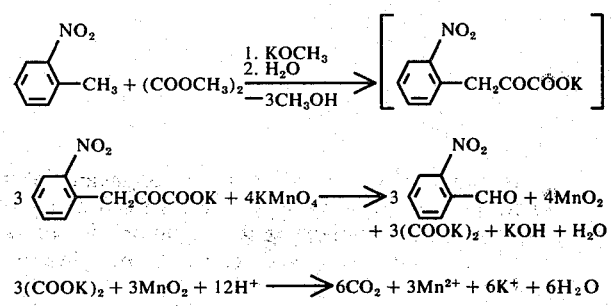

The oxidation with potassium permanganate (component IV → I) can be carried out in aqueous solution and the resulting 2-nitrobenzaldehyde can be isolated by extraction. However, preferably an additional water-immiscible solvent (forming a two-phase system) is present from the start.

The term alkali metal preferably denotes sodium or potassium. In the formula III, (COOR)$_2$, R preferably represents alkyl with 1 to 6 carbon atoms, especially methyl, ethyl, propyl, isopropyl, n-butyl, tert.-butyl, pentyl and hexyl, or represents benzyl.

Preferably, the reaction solution is acidified with sulphuric acid. Other acids such as hydrochloric acid are entirely operable but may undergo undesirable chemical reactions with manganese-(IV) oxide such as the formation of toxic chlorine gas.

The reaction Iv → I is carried out at temperatures between −10° and +50° C, preferably between −2° and +30° C.

2-nitrobenzaldehyde is used, inter alia, as an intermediate for the preparation of coronary-dilating pharmaceuticals, especially 1,4-dihydropyridines; see, e.g., German Offenlegungsschrift 1,670,827.

The following examples will serve to further typify the nature of the invention without being a limitation on the scope thereof.

EXAMPLE 1

383 g (7.1 mols) of sodium methylate are dissolved in ethanol and 985 g (6.75 mols) of oxalic acid diethyl ester and 925 g (6.75 mols) of 2-nitrotoluene are poured in. The mixture is heated under reflux for 30 minutes and is allowed to cool, 300 ml of ice water are next added cautiously and after the exothermic reaction has subsided 1,600 ml of water are added. After boiling additionally for 90 minutes under reflux, the mixture is steam-distilled until two phases no longer pass over. The organic phase is separated from the distillate and 310 g of 2-nitrotoluene are recovered from it. The residual aqueous phase of the distillate is filtered, 600 g of (anhydrous) sodium carbonate and 2,000 ml of toluene are added and the mixture is cooled to +3° C. 650 g of solid potassium permanganate are added over the course of 70 minutes and the reaction temperature is kept at between +2° and +6° C. The mixture is stirred for a further 45 minutes at +5° C and then warmed to 40° C, and 50% strength sulphuric acid is then added dropwise (gas being evolved). The exothermic reaction is kept at 35°– 40° C by cooling. Insoluble material is then filtered off and the toluene phase is separated from the filtrate. The filter residue is washed with hot toluene and the combined toluene phases are extracted by shaking with 15% strength sodium carbonate solution and with water and are then dried with the sodium sulphate. On concentrating the toluene phase in vacuo, 2-nitrobenzaldehyde is obtained as a viscous oil which crystallizes immediately on cooling. Melting point 40°– 41° C.

Yield 272 g (40.3% of theory, based on 2-nitrotoluene converted).

EXAMPLE 2

50 g (0.24 mol) of 2-nitrophenylpyruvic acid of melting point 115° C are introduced into 500 ml of aqueous sodium carbonate solution until a clear solution is obtained. After addition of 350 ml of toluene, the mixture is cooled to 0° C and 4 g of solid potassium permanganate are then added in portions at 0°– 3° C. After one hour at 0°– 3° C, 95 ml of 50% strength sulphuric acid are added dropwise and the temperature is not allowed to rise above 30° C. The reaction mixture is filtered and the toluene phase is separated from the filtrate. The filter residue is washed with toluene and the combined toluene phases are extracted with 15% strength sodium carbonate solution and with water. The toluene phase is then dried with sodium sulphate and concentrated in vacuo. The residue which remains consists of 19.7 g (54.7% of theory) of 2-nitrobenzaldehyde, which crystallizes on cooling. Melting point 41° C.

What is claimed is:

1. The process for the preparation of 2-nitrobenzaldehyde wherein 2-nitrotoluene is treated with a diester of oxalic acid in the presence of an alkali metal alcoholate to yield the alkali metal salt of 2-nitrophenylpyruvic acid, said salt is treated with solid potassium permanganate at a temperature of from about −10° to about 50° C in a binary solvent system comprising water and a water immiscible organic solvent for 2-nitrobenzaldehyde, and said 2-nitrobenzaldehyde is separated from said reaction mixture in said water immiscible solvent.

2. The process according to claim 1 wherein said treatment with potassium permanganate is effected at a temperature of from about −2° to about +30° C.

3. The process according to claim 1 wherein the potassium permanganate reaction solution is acidified to reduce manganese-(IV) oxide to soluble manganese-(II) salts and convert oxalic acid to carbon dioxide.

4. The process according to claim 3 wherein the reaction solution is acidified with sulphuric acid.

5. The process according to claim 1 wherein the alkali metal salt of 2-nitrophenylpyruvic acid is the sodium salt.

6. The process according to claim 1 wherein the diester of oxalic acid is the diethyl ester.

* * * * *